(12) United States Patent
Doty

(10) Patent No.: US 7,697,706 B2
(45) Date of Patent: Apr. 13, 2010

(54) LOW SOUND ATTENUATING HEARING PROTECTION DEVICE

(75) Inventor: Marc Doty, Brownsburg, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 987 days.

(21) Appl. No.: 10/700,213

(22) Filed: Nov. 3, 2003

(65) Prior Publication Data

US 2005/0094835 A1    May 5, 2005

(51) Int. Cl.
*H04R 25/00* (2006.01)
*A61F 11/00* (2006.01)

(52) U.S. Cl. .................. 381/328; 381/322; 381/312; 128/864

(58) Field of Classification Search ............ 381/72, 381/312, 322, 328; 128/864
See application file for complete search history.

(56) References Cited

U.S. PATENT DOCUMENTS

| | | | |
|---|---|---|---|
| 3,080,011 A * | 3/1963 | Henderson .................. | 181/135 |
| 3,131,241 A | 4/1964 | Mendelson | |
| 3,800,791 A | 4/1974 | Visor | |
| 4,441,576 A | 4/1984 | Allen | |
| 4,461,290 A * | 7/1984 | Gardner et al. .............. | 128/866 |
| 4,540,063 A | 9/1985 | Ochi et al. | |
| 4,807,612 A | 2/1989 | Carlson | |
| 4,852,683 A | 8/1989 | Killion | |
| 4,867,149 A | 9/1989 | Falco | |
| 5,113,967 A | 5/1992 | Killion et al. | |
| 5,188,123 A | 2/1993 | Gardner, Jr. | |
| 5,936,208 A * | 8/1999 | Hamery ...................... | 181/135 |
| 6,095,146 A | 8/2000 | Knauer et al. | |
| 6,105,715 A | 8/2000 | Knauer | |
| 6,148,821 A * | 11/2000 | Falco ......................... | 128/864 |
| 6,826,287 B2 * | 11/2004 | Myers ........................ | 381/373 |
| 6,938,622 B2 | 9/2005 | Huang | |
| 2002/0080979 A1 * | 6/2002 | Brimhall et al. ............... | 381/72 |

FOREIGN PATENT DOCUMENTS

| | | |
|---|---|---|
| DE | 4217 043 | 11/1992 |
| DE | 101 58 648 | 6/2003 |
| FR | 1 160 357 | 7/1958 |
| FR | 1 326 407 | 5/1963 |
| TW | 92129573 | 12/2003 |

OTHER PUBLICATIONS

International Search Report; PCT/US2004/036715; Mar. 15, 2005.

* cited by examiner

*Primary Examiner*—Vivian Chin
*Assistant Examiner*—George C Monikang
(74) *Attorney, Agent, or Firm*—Karl G. Hanson

(57) ABSTRACT

A hearing protection device and a method of manufacturing thereof is provided. The device includes a sound attenuating portion for being disposed within an ear canal of a user to obstruct the passage of sound and a channel formed through the sound attenuating portion for allowing sound to pass through the sound attenuating portion.

54 Claims, 8 Drawing Sheets

LOW SOUND ATTENUATING HEARING PROTECTION DEVICE

TECHNICAL FIELD OF INVENTION

The invention concerns hearing protection devices and, more particularly, hearing protection devices which provide a low sound attenuation.

DESCRIPTION OF RELATED ART

Hearing protection devices, such as earplugs and semi-aural devices, are readily used to provide sound attenuation. Such devices are inserted into the ear canal of a user, or placed over the opening of the ear canal, to physically obstruct the passage of sound waves into the inner ear.

Earplugs include any of a variety of devices designed to be inserted in the ear canal of a user and worn therein to prevent sounds from entering. Push-in type earplugs comprise an attenuating portion and a rigid or semi-rigid portion typically extending therefrom or embedded therein. The sound attenuating portion may be a rubber, plastic, or foam material; the rigid or semi-rigid portion may be composed of any material, such as a plastic or a rubber, with sufficient rigidity as required. To insert the push-in type earplug, the user grasps the rigid/semi-rigid portion (or an end of the earplug proximate thereto), positions the earplug proximate the ear canal opening, and inserts the sound attenuating portion into the canal by pushing with the rigid/semi-rigid portion. The sound attenuating portion compresses, as necessary, upon entry into the ear canal and is held therein by a friction fit occluding the canal and thus attenuating sound.

Such a push-in type earplug may be found, for example, in U.S. Pat. Nos. 4,867,149 and 5,188,123 to Falco and Gardner Jr., respectively, which are herein incorporated by reference in their entirety.

Roll-down type earplugs are also known. Such earplugs simply comprise a compressible, resilient body portion made of a rubber, plastic, or, preferably, a foam material. The body portion is typically cylindrical or semi-cylindrical in shape and includes a circular cross-section having a diameter greater than that of the ear canal of a user. Insertion is accomplished by, first, compressing the body portion to a diameter less than that of the ear canal, second, pushing the body portion therein, and, third, allowing the same to decompress slightly to fill the ear canal, thus obstructing the ear canal and preventing passage of sound.

Such roll-down type earplugs may be found, for example, in U.S. Pat. No. 6,105,715 to Knauer, which is herein incorporated by reference in its entirety.

Semi-aural devices comprise a curved band having first and second ends and a sound attenuating element disposed at each of said first and second ends. The curved band is generally composed of a rigid or semi-rigid plastic or rubber material while the sound attenuating elements are formed of a compressible resilient material such as a rubber, a plastic, or a foam-like material. The sound attenuating elements are generally inserted into the ear canal of the user by the push-in technique described above with reference to push-in type earplugs. When the sound attenuating elements are properly inserted into the ear canal, the curved band attaching the elements may be worn by the user as desired, for example, over the head, under the chin, behind the neck, etc. Such a semi-aural device is described, for example, in U.S. Pat. No. 4,461,290 to Gardner, which is herein incorporated by reference in its entirety.

The described hearing protection devices have been designed and developed to provide a high degree of sound attenuation. Where a proper fit of the device is obtained, in many cases, nearly a complete attenuation of sound results. For example, roll-down type earplugs commercially available under the trademarks EAR Classic and EAR Ultrafit provide sound attenuation having a Single Number Rating (SNR) of approximately 28 dB and 32 dB, respectively.

Often, however, a lower sound attenuation is desired. That is, applications exist where a user desires sound to penetrate the hearing protection device and pass through the ear canal to the inner ear. In this way, a degree of hearing protection may be provided but the user is still permitted to hear sounds.

A hearing protection device with such characteristics is desired, for example, in moderately loud industrial settings where it behooves a user to hear workplace noises while still being provided with a level of hearing protection. For instance, a worker on a manufacturing floor may desire to hear voice communication from a colleague or sounds from a moving truck, etc. In such an instance, full or nearly full sound attenuation provided by many common earplugs is not desirable. Thus, a lower attenuating plug is needed.

Hearing devices, particularly earplugs, are known in the art which include provisions for reducing attenuating levels. See, for example, U.S. Pat. Nos. 4,441,576, 4,540,063, 5,113,967, and 6,148,821 to Allen, Ochi, Killion, and Falco, respectively. However, these and similar attempts require a damping device at the interior of the earplug and/or a complicated network of damping passageways disposed within the earplug. Hence, the construction of such earplugs is quite complex making manufacture difficult and, often, cost prohibitive. Further, the damping devices and/or passageways are easily clogged, broken, or otherwise comprised during use, thus requiring frequent maintenance and/or replacement.

Also, considerable difficulty has been found in producing an effective low attenuation earplug. That is, while many earplugs have been developed which provide high degrees of attenuation, a plug which effectively and consistently provides a low attenuation has been difficult to achieve. This is mainly because any airway through or around an earplug constitutes a leak which is known to dramatically affect the performance of the earplug. Thus, many attempts at producing a low attenuation earplug have simply resulted in a plug with near zero attenuation.

Accordingly, a hearing protection device is desired which consistently and effectively provides a low sound attenuation to a user's ear and which is easy to manufacture, is cost efficient, and durable.

BRIEF SUMMARY OF THE INVENTION

The above discussed and other problems and deficiencies of the prior art are overcome or alleviated by the invention which provides a hearing protection device and a method of manufacturing thereof. The device includes a sound attenuating portion for being disposed within an ear canal of a user to obstruct the passage of sound and a channel formed through the sound attenuating portion for allowing sound to pass through the sound attenuating portion.

BRIEF DESCRIPTION OF THE DRAWINGS

Referring now to the drawings wherein like elements are numbered alike in the several FIGURES.

DETAILED DESCRIPTION OF THE INVENTION

Figure 1:
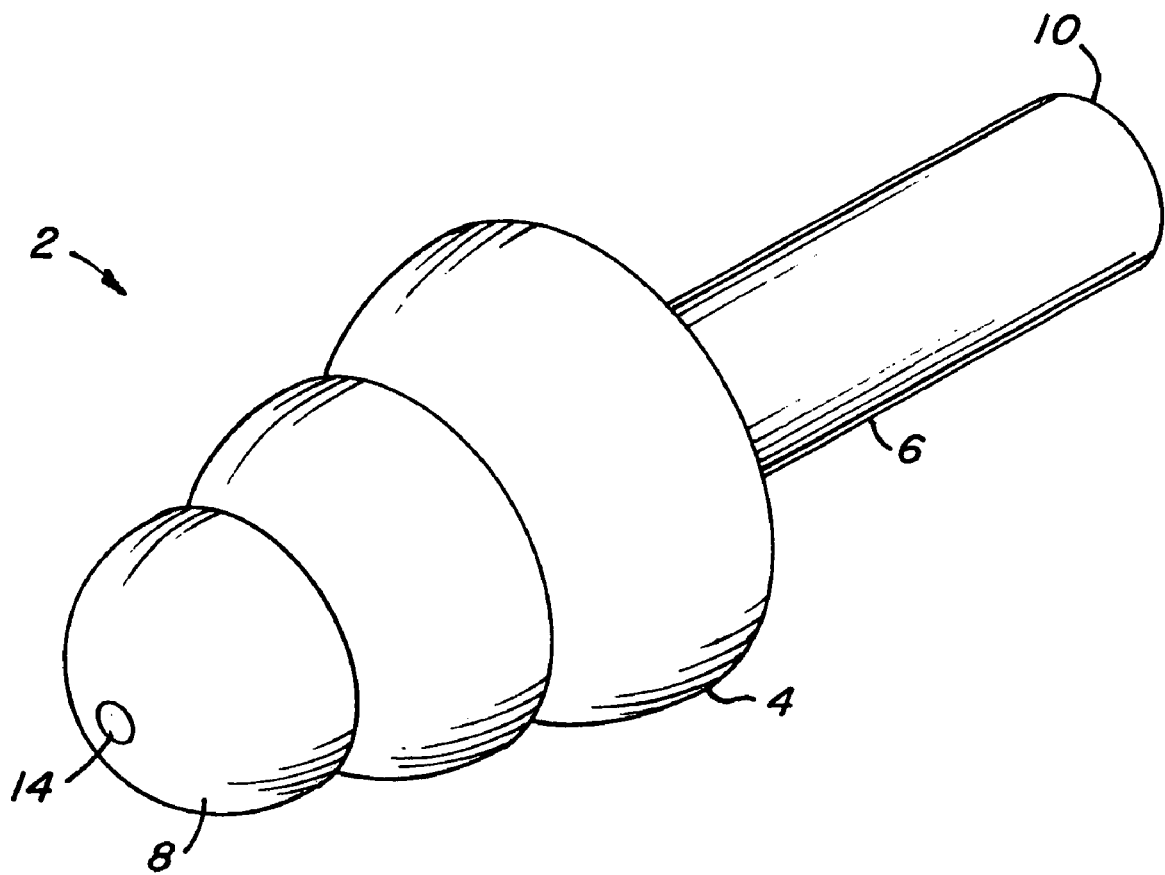
FIG. 1 is a perspective view of an earplug in one embodiment of the invention.
Figure 2:
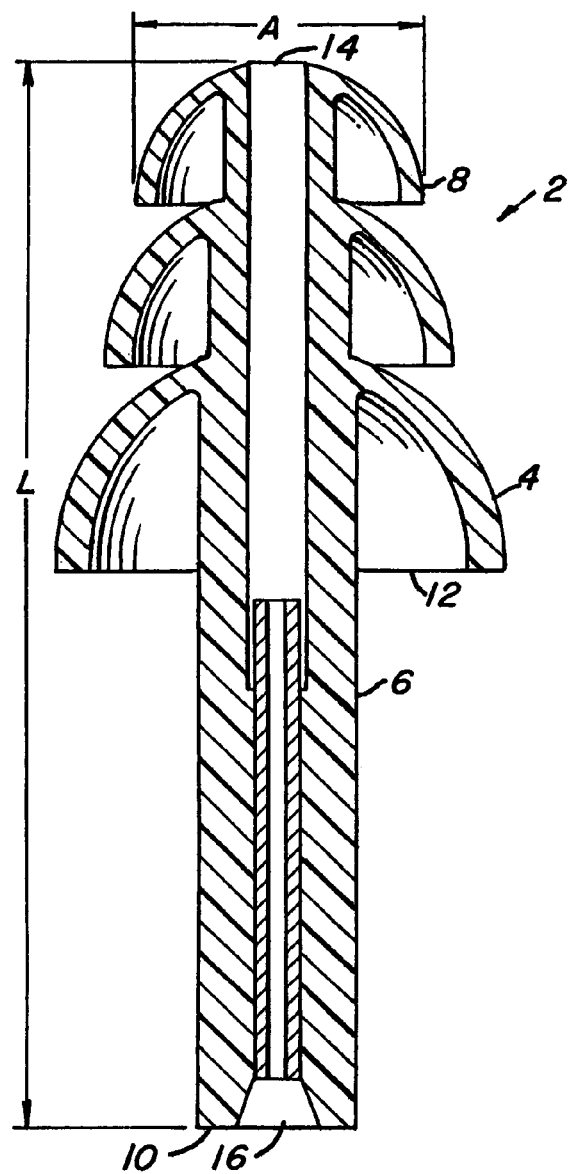
FIG. 2 is a cross-section view of the earplug of FIG. 1.
Figure 3:
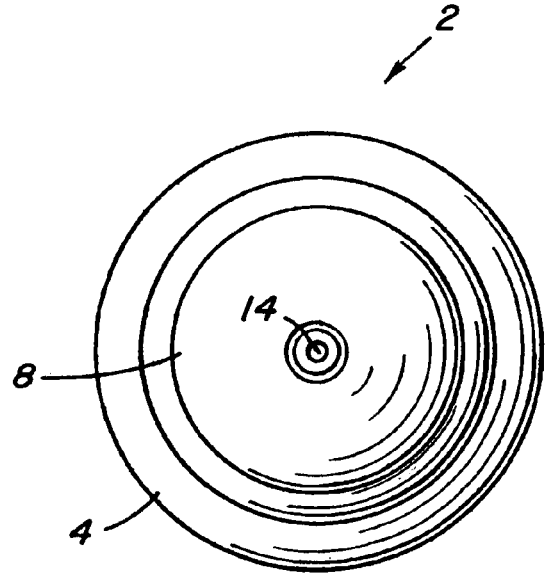
FIG. 3 is a front elevational view of the earplug of FIG. 1.

FIGS. 1, 2, and 3 show a hearing protection device in one embodiment of the invention. Particularly, an earplug 2 is shown including flanges 4 emanating from an elongated stalk member 6. The stalk member 6 has a first end 8 from which a first of the flanges 4 emanates and an opposing second end 10 which extends longitudinally beyond the flanges 4. The flanges 4 are substantially hemispherical in shape and extend in a direction toward the second end 10 of the stalk member 6 such that spaces 12 are formed between a back side of the flanges 4 and the stalk member 6. Each of the plurality of flanges 4 includes a substantially circular cross-section A. The flanges 4 are variously sized such that the cross-section A of the flange 4 proximate the first end 8 of the stalk member 6 is the smallest with each successive flange 4 having a larger cross-section A.

The stalk member 6 further includes a channel 14 formed therethrough along a longitudinal axis of the earplug 2. That is, the channel 14 extends through the stalk member 6 from the first end 8 to the second end 10. The channel opens to an exterior of the earplug 2 at the first and second ends 8, 10 of the stalk member 6. In a preferred embodiment, the channel 14 is substantially cylindrical in shape.

The earplug 2 further comprises a tube 16 disposed within the earplug 2 at the channel 14. That is, the tube 16 is fixed to the earplug 2, and more particularly, to an interior of the stalk member 6 at the channel 14. The tube 16 is hollow with a substantially cylindrical shape and may be positioned within the earplug 2 to extend from, be flush against, and/or recede into each of the first and second ends 8, 10 of the stalk member 6. In a particularly preferred embodiment, as shown in FIG. 2, the tube 16 includes one end set approximately flush against the second end 10 of the stalk member 6 and an opposing end disposed proximate the largest of the flanges 4.

The earplug 2 is generally composed of a resilient polymeric material and may be formed by any suitable conventional manufacturing techniques including, preferably, injection molding. The resilient polymeric material has a Shore A Durometer hardness value sufficient to provide the flanges 4 with a desired degree of pliability. The stalk member 6 may be formed of the material so as to possess higher hardness value thus providing a degree of rigidity to the earplug 2.

There are many known resilient polymeric materials which may be utilized effectively in the fabrication of the earplug 2 including, but not limited to, natural rubber, neoprene rubber, SBR rubber, silicone rubber, EPDM rubber, polybutadiene rubber, polyurethane elastomers, vinyl halide polymers, etc.

The tube 16 may be composed of any suitable material for providing the tube 16 with desired pliability, semi-rigidity, or rigidity. For example, the tube may be made of a polyetheretherketone (PEEK), a metal, a natural or synthetic rubber material, or a plastic material such as polyethylene, PVC, nylon, vinyl, etc., or combinations thereof.

The tube 16 is fixed to the interior of the stalk member 6 at the channel 14, preferably, by a friction fit. As mentioned, both the channel 14 and the tube 16 are substantially cylindrical in shape. The tube 16 includes an outer diameter $D_O$ and an inner diameter $D_I$. The outer diameter $D_O$ of the tube 16 is the diameter of the tube 16 measured from its outer surfaces, that is, those surfaces of the tube 16 which contact the earplug 2. The inner diameter $D_I$ of the tube 16 is the diameter of the tube measured from its inner surfaces, that is, those surfaces which do not contact the earplug 2. To provide the desired friction fit of the tube 16 within the channel 14, the outer diameter $D_O$ of the tube 16 is sized slightly larger than the diameter of the channel 14. Thus, when the tube 16 is inserted in the channel 14 the resilient polymeric material composing the portion of the stalk member 6 proximate the channel 14 is slightly displaced causing a compression/tension situation therein which creates the desired friction fit between the earplug 2 and the tube 16.

Alternatively, the tube 16 may be fixed to the earplug 2 at the channel 14 with a bonding agent. For example, a glue may be applied to the tube 16 and/or the channel 14 prior to the insertion of the former into the latter. Then, upon curing of the glue, the tube 16 is firmly bonded to the resilient polymeric material of the earplug 2.

In another alternate embodiment, the stalk member 6 may be formed about and bonded to the tube 16 such that the tube 16 is fixed along a longitudinal axis of the stalk member 6. That is, the stalk member 6 may be formed by, for example, injection molding. In such process, the resilient polymeric material is inserted in a liquidous form into a mold in which the tube 16 is predisposed. The liquidous polymeric material fills the mold around the tube 16 and is allowed to cure or set. The curing process allows the polymeric material to bond with the outer surface of the tube 16. Once completed, the stalk member 6 is ejected from the mold. Resultantly, the tube is permanently fixed within the stalk member 6. The flanges 4 may be injection molded along with the stalk member 6 or in a subsequent processing step.

As mentioned, the earplug 2 is formed by any suitable resilient polymeric material. The earplug 2 and/or parts thereof may be manufactured by any suitable process including, but not limited to, injection molding (see above), casting, extrusion, etc.

In use, the second end 10 of the stalk member 6 acts as a handle which is gripped by a user during insertion. The earplug 2 is brought proximate the user's ear and then inserted into the ear canal. The first end 8 of the stalk member 6, and the smallest of the flanges 4 disposed there at, enters the ear canal first during insertion. Then, the earplug 2 is pushed into the canal by the second end 10 of the stalk member 6. The flanges 4 compress slightly during insertion and lodge in the ear canal to significantly block the passage of sound. A portion of the second end 10 of the stalk member 6 remains at the opening of the ear canal or slightly extending therefrom to act as a handle for removing the earplug 2.

The tube 16, as disposed in the stalk member 6, in combination with the channel 14, form a pathway through the earplug 2 such that, when the earplug 2 is properly inserted as described, a narrow column of air exists between the user's inner ear and the outer environment. This column of air essentially comprises a leak in the occlusion provided by the earplug and thus allows sound to penetrate the earplug and reach the auditory organs in the user's inner ear. In this way, a low attenuation is provided by the earplug such that, when properly inserted, the user hears sound from the outer environment but still is provided with a degree of hearing protection.

The transmission of sound through the pathway created by the tube 16 is dependent upon, among other things, the volume of the column of air formed within the tube 16. That is, at least a diameter and a length of the column are critical parameters for the transmission of sound. The column of air, of course, is delimited by inner dimensions of the tube. Thus, correspondingly, the inner diameter $D_I$ of the tube 16 and a length L of the tube 16 are both designed to specifically delimit the resulting column of air as desired for a chosen sound propagation.

The inner diameter $D_I$ is generally in the range of approximately 0.005 inch to approximately 0.050 inch. The corresponding length L is approximately 1.00 inch to approximately 0.100 inch, respectively. More particularly, in one preferred embodiment, the inner diameter $D_I$ is approximately 0.030 inch and the length L is approximately 0.256 inch. In another embodiment, the inner diameter $D_I$ is approximately 0.020 inch and the length L is approximately 0.500 inch.

Compression or other deformation of the tube 16 during, for example, insertion of the earplug 2 into the ear canal of the user is clearly undesirable because such deformation of the tube 16 would result in corresponding deformation of the air column delimited thereby. Thus, the material(s) used to manufacture the tube 16 (see above) must be suitable to maintain the shape and dimensions thereof during ordinary use and handling of the earplug 2. For example, the tube 16 may be manufactured of a rigid or semi-rigid rubber or plastic material.

Additionally, the tube 16 is preferably placed in the channel 14 proximate the second end 10 of the stalk member 6, as shown by example in FIG. 2. This feature provides many advantages, including disposing the tube 16 so as to limit the compression forces exerted thereon when the earplug 2 is inserted into the earcanal. That is, during insertion, the flanges 4 are received within the earcanal and the second end 10 of the stalk 6 is positioned at the opening of the earcanal or extending therefrom. Thus, the flanges 4, not the second end 10 of the stalk member 6, receive the majority of compression forces associated with insertion of the earplug 2.

Additionally a comfort advantage is derived from disposing the tube 16 proximate the second end 10 of the stalk member 6. Particularly, the rigid or semi-rigid nature of the tube 16 does not effect a user while wearing the earplug 2 because, as mentioned above, the second end 10 of the stalk member does not generally lie within the earcanal when the earplug 2 is inserted. Thus, the user is only exposed to the comfortable, pliable nature of the first end 8 of the stalk member 6.

The portion of the channel 14 not buttressed by the tube 16 may be reinforced, as discussed herein, to counter the compressive forces of insertion. Alternatively, such channel may not include reinforcement and thus may compress slightly during insertion and/or use. However, the invention contemplates such condition and thus sizes the channel 14 appropriately such that compression of the channel 14 does not inhibit the desired passage of sound. That is, the pathway of sound or the 'leak' is maintained even during compression of the channel 14 due to the appropriately sized channel diameter.

As mentioned, the tube 16 is preferably fixed within the earplug 2 at the channel 14 by a simple friction fit. The friction fit enables a simple manufacture of the earplug 2 and is also cost effective. Further, it is noted that the friction fit enables the tube 16 to be selectively removed by the user from the stalk member 6, if desired. In this way, the tube 16 may be easily replaced if deformed or otherwise malfunctioning. Further, the selective removability of the tube 16 allows for easy cleaning and maintenance of the tube 16, thus extending the overall life of the earplug 2.

While this embodiment of the invention has been described as including the tube 16 friction fit within the channel 14, the invention clearly contemplates other embodiments wherein, for example, there is no such tube 16. That is, in an alternate embodiment, the earplug 2 includes the channel 14 having appropriate inner dimensions to form the desired column of air extending through the earplug 2. Such earplug 2 may include a reinforcement zone proximate the channel 14 to provide a degree of rigidity to the column 14 to thus prevent compression or collapse thereof during insertion of the earplug 2 into the ear canal of the user. The reinforcement zone may comprise an area of the resilient compressible material having a high density and/or a high Shore A Durometer hardness value and may further extend partially or entirely along the channel 14.

Accordingly, in this embodiment, the channel 14 itself maintains the column of air through the length of the earplug 2 and forms a pathway from the outer environment to the inner ear of the user to thus transmit sound to the inner ear. Such embodiment of the earplug 2 may be manufactured by any suitable conventional means including, but not limited to, single or multi-step injection molding, casting, extrusion, etc.

The earplug 2, as shown and described herein, may further include a stem (not shown) embedded in and/or extending from the stalk member 6. The stem may be used: to provide a degree of rigidity to the stalk member; as a handle to facilitate insertion and removal of the earplug 2 from the ear canal of the user; to connect a cord or other device to the earplug; etc. The stem is disposed along the longitudinal axis of the earplug 2. Thus, the channel 14 extends through portions of the stalk member and through at least a portion of the stem. Such a stem is composed of a rigid or semi-rigid material such as a synthetic or natural rubber, a plastic, etc.

Figure 4:
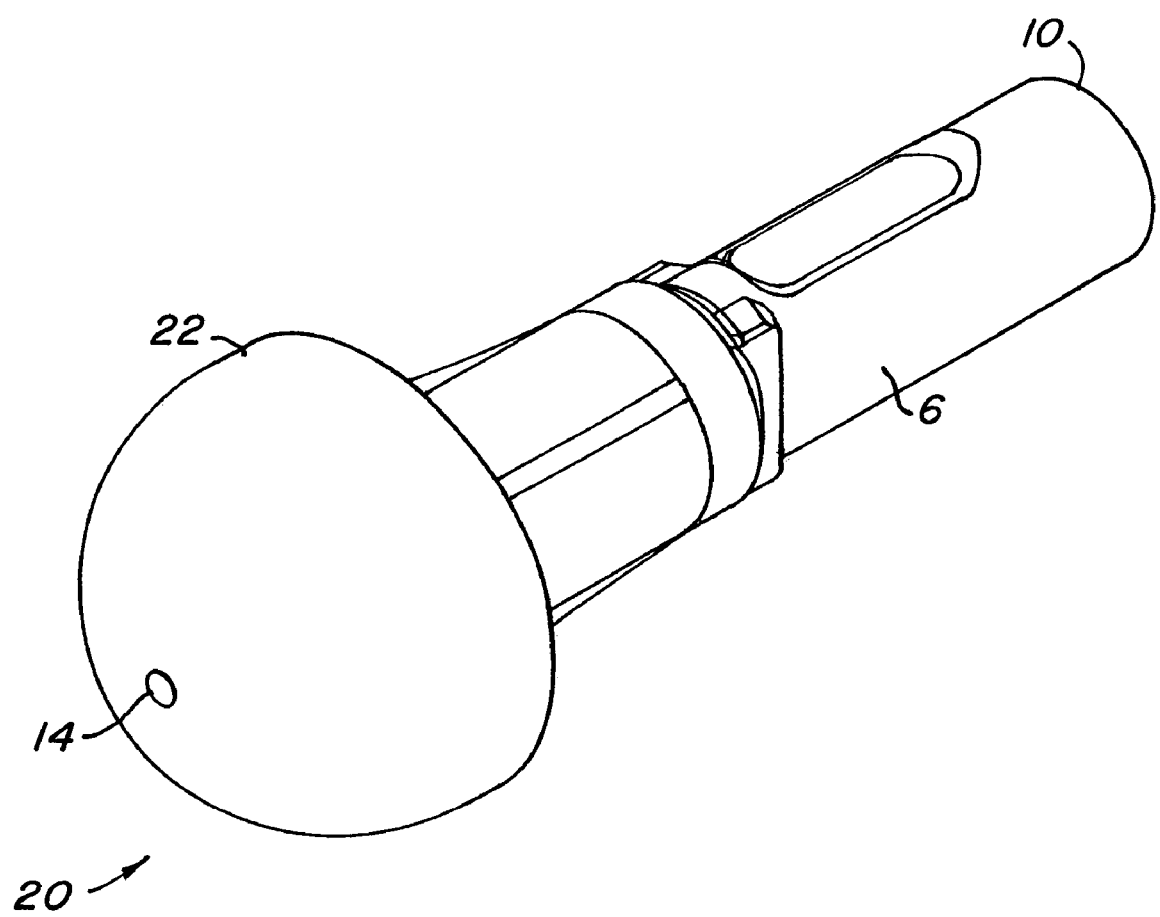
FIG. 4 is a perspective view of an earplug in a second embodiment of the invention.
Figure 5:
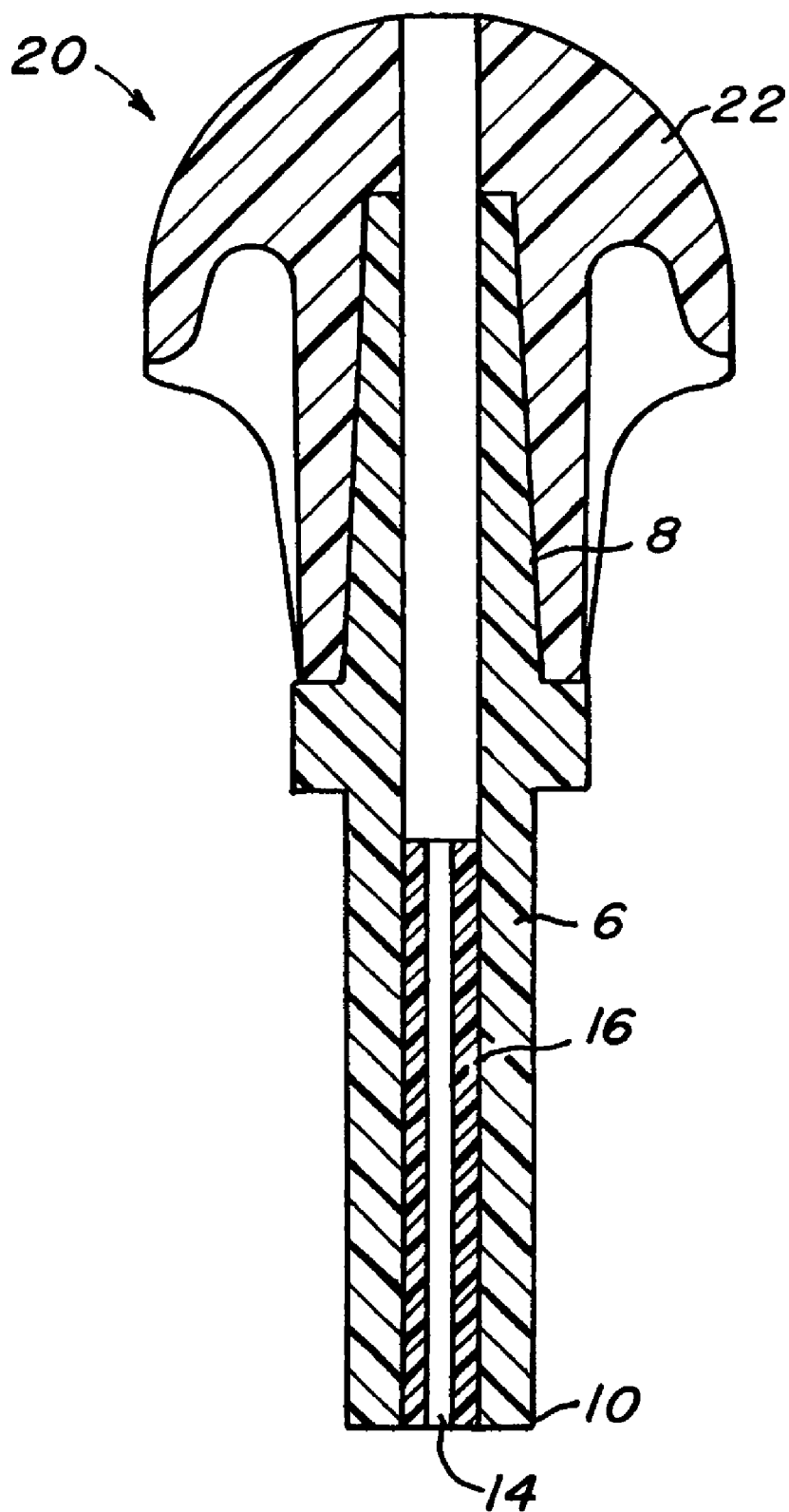
FIG. 5 is a cross-section view of the earplug of FIG. 4.

FIGS. 4-5 show an earplug 20 according to another embodiment of the invention. Please note, like parts and components are indicated herein and throughout with consistent reference numerals.

The earplug 20 includes a sound attenuating portion 22 disposed at the first end 8 of the elongated stalk member 6. The sound attenuating portion 22, generally, is any item which is insertable into the ear canal of a user and suitable for blocking and/or damping sound traveling through the ear canal. More specifically, as shown in FIGS. 3-4, the sound attenuating portion 22 is a substantially hemispherical lobe which extends rearwardly toward the second end 10 of the stalk member 6.

The earplug 20 further includes the channel 14 extending along a longitudinal axis of the earplug 20 through the stalk member 6 and through the sound attenuating element 22 such that the channel opens to the outer environment at an insertion surface 24 of the sound attenuating element 22 and at the second end 10 of the stalk member 6. The tube 16 is disposed within the earplug 20 at the channel 14 and held therein, preferably, by a friction fit which results due to the outer diameter $D_O$ of the tube 16 being slightly larger than the diameter of the channel 14. The tube 16 may extend the exact length of the channel 14, as shown, or may possess a length L less than or greater than the length of the channel 14. In a preferred embodiment, as shown in FIG. 5, the tube 16 is substantially shorter than the channel and is disposed proximate the second end 10 of the stalk member 6.

The stalk member 6, as mentioned above, is made of any suitable pliable, semi-rigid, or rigid material as is desired. Particularly, the stalk member 6 may be composed of a plastic or a rubber material and may be formed, preferably, by injection molding.

The sound attenuating portion 22 is made, preferably, of a compressible resilient material such as, for example, a compressible resilient plastic or rubber material or composition. Preferably, the sound attenuating portion is composed of a foam-like material composed of a soft, pliable self-rising foam with instant recovery properties such as a polyurethane or an acrylic blend foam. Other suitable foams include PVC, silicone, and nitrile, among others. A suitable foam is described, for example, in U.S. Pat. No. 5,792,998 to Gardner, Jr. et al., herein incorporated by reference. The earplug described therein is comprised of a dynamically stiff foam material having a low static stiffness, and a high dynamic stiffness. Another suitable foam is described, for example, in U.S. Pat. No. 4,158,087 to Wood, herein incorporated by reference.

The sound attenuating portion 22 may be formed, for example, by a molding process and then bonded on the first end 8 of the stalk member 6 by bonding agent such as a glue.

In use, the earplug 20 is handled by the second end 10 of the stalk member 6 and brought proximate the ear of a user. Then, the sound attenuating element 22 is inserted into the opening of the ear canal and inserted into the canal by pushing on the second end 10 of the stalk member 6. The sound attenuating element 22 compresses within in the ear canal and lodges therein to attenuate the passage of sound from the outer environment to the inner ear. The second end 10 of the stalk member 6 remains at or extends from the ear canal when the earplug 22 is full inserted. To remove the earplug 20, the user grasps the exposed second end 10 and pulls the earplug 20 from the ear canal.

As mentioned, the compressed sound attenuating portion 22 lodged in the ear canal provides attenuation, however, sound is permitted to reach the inner ear via the column of air formed and maintained by the tube 16 fixed within and extending through the earplug 20.

Here again, as described above with reference to FIGS. 1, 2, and 2A, the inner diameter $D_I$ of the tube 16 is approximately 0.005 inch to approximately 0.050 inch; the length L is approximately 0.100 inch to approximately 1.000 inch; and, more particularly, in one exemplary embodiment, the inner diameter $D_I$ is approximately 0.030 inch and the length L is approximately 0.256 inch, and in another embodiment $D_I$ is approximately 0.020 inch and L is approximately 0.500 inch. Also as mentioned, the tube is constructed of a suitable material such that the column of air is maintained even under the pressures and constraints of earplug insertion.

Additionally, while the earplug 20 has been described thus far as including the tube 16, the invention contemplates an embodiment of the earplug 20 without the tube 16 where the channel 14 is sized as desired to delimit the required column of air. In such embodiment, the earplug 20 may be reinforced in some manner proximate the channel 14 so as to maintain the precise configuration of the column of air during use and handling of the earplug 20. Such reinforcement may be disposed along the entire length of the channel 14 or only partially.

Figure 6A:
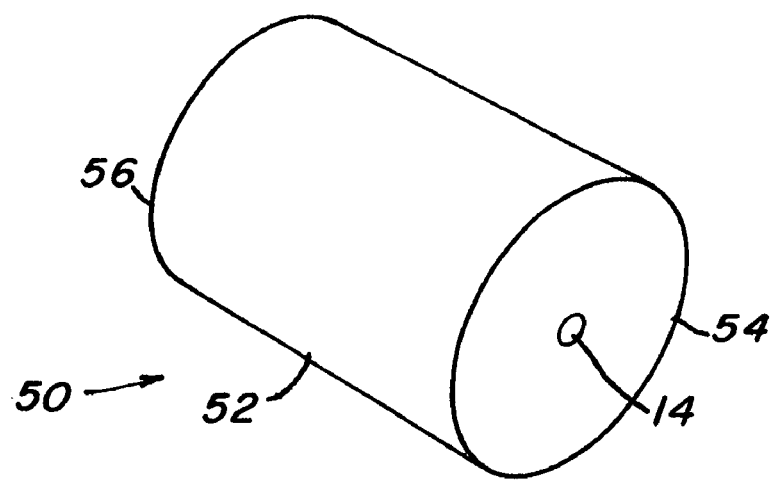
FIGS. 6A and 7A show perspective and cross-section views, respectively, of an earplug in a third embodiment of the invention.
Figure 7A:
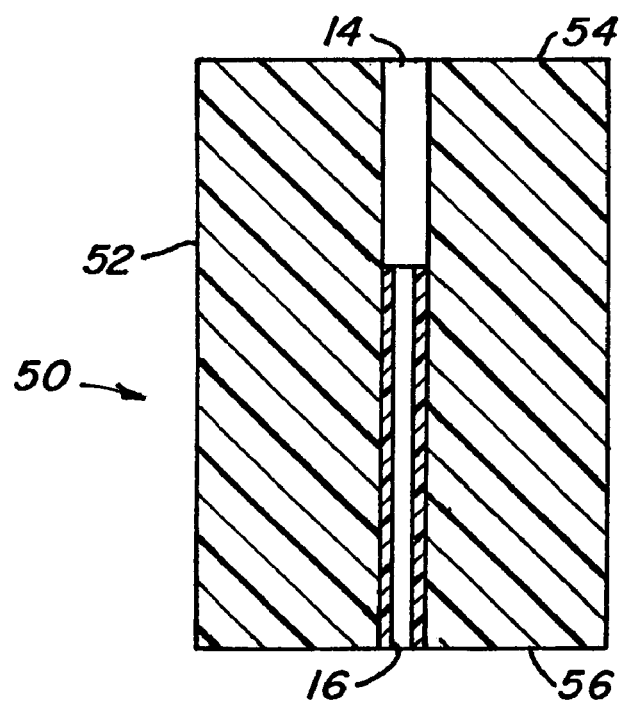

FIGS. 6A and 7A show an earplug 50 in another embodiment of the invention. The earplug 50 includes a body portion 52 having a first end 54 and an opposing second end 56. Additionally, the earplug 50 includes the channel 14 formed along a longitudinal axis thereof, from the first end 54 to the second end 56. The tube 16 is disposed within the channel and fixed therein to the body portion 52. The tube 16, as described previously, is preferably friction fit in the channel 14 but may be adhered or bonded as well.

The earplug 50 is formed of a compressible resilient material, such as, for example, a foam-like material. More particularly, the earplug 50 is composed preferably of a foam made of a polyurethane, an acrylic blend, a PVC, a silicone, a nitrile, etc. The earplug 50 may be formed by any suitable conventional manufacturing process including, but not limited to, molding, extrusion, die casting, etc.

The channel 14 may be formed at the time of manufacturing the body portion 52 or in a separate subsequent processing step. For example, where the body portion 52 is formed by molding, the pertinent mold includes an insert disposed therein which the body portion 52 forms about in order to form the channel 14. That is, the foam material, in a liquidous form, is injected into the mold. The insert is, for example, a pin shaped element extending within the mold. The foam material is allowed to expand and fill the mold around the insert. Once the foam is fully formed, the new body portion 52 is ejected from the mold. During ejection, the insert is removed from the body portion thus resulting in formation of the channel 14.

Alternatively, of course, the channel 14 may be made in a separate processing step. That is, the body portion 52 may be manufactured first and then the channel may be formed subsequently by, for example, drilling, etching, laser treatment as described in U.S. patent application Ser. No. 10/346,604 to Taylor herein incorporated by reference in its entirety, water jet treatment as described in U.S. patent application Ser. No. 10/660,015 to Schreiber herein incorporated by reference in its entirety, etc.

After formation of the body portion 52 and the channel 14, the tube 16 is inserted into the channel 14 and fixed therein to the body portion 52. As discussed previously, the tube is composed of a rubber or plastic material with sufficient strength to withstand the pressures of handling and use of the earplug 50. Here again, the tube 16 may have a length greater or less than a length of the channel 14. Preferably, the length of the tube 16 is substantially less than the length of the channel 14 and is disposed proximate the second end 56 of the earplug 50, as shown in FIG. 7.

In use, the earplug 50 is first compressed to reduce a cross-sectional diameter thereof. Preferably, this is accomplished by the user rolling the earplug 52 between the fingers or hands about the longitudinal axis of the plug. This rolling/compression technique is applied until the diameter of the earplug 50 is approximately less than a diameter of the user's ear canal. Then, the first or second end 54, 56 of the earplug 50 is inserted through the opening of the ear canal and into the canal. The earplug 50 is inserted in the ear canal to a depth such that the trailing end 54, 56 of the body portion 52 is at or extending slightly from the opening of the ear canal. Once inserted into the ear canal, the resilient material composing the earplug 50 expands from its temporarily compressed state to fill the ear canal and lodge the earplug 50 therein, thus effectively attenuating the passage of sound.

However, while a significant degree of sound attenuation is achieved by the body portion 52 of the earplug 50, the tube 16 extending through the core of the body portion 52 delimits a column of air connecting the auditory organs of the inner ear to the outer environment. Thus, sound is permitted to travel from the outer environment through the tube 16 to the inner ear. In this way, the earplug 50 provides the user with a degree of hearing protection while still allowing sound to be heard, thus providing a low attenuation.

The inner diameter $D_I$ of the tube 16 is approximately 0.005 inch to approximately 0.050 inch; the length L is approximately 0.100 inch to approximately 1.000 inches; and, more particularly, in one exemplary embodiment, the inner diameter $D_I$ is approximately 0.030 inch and the length L is approximately 0.256 inch, and in another embodiment, $D_I$ is approximately 0.020 inch and L is approximately 0.500 inch.

As with other embodiments of the invention discussed herein, the earplug 50 has been described thus far as including the tube 16. Nonetheless, the invention clearly contemplates the earplug 50 as not including the tube 16. Such embodiment of the earplug 50 would include the channel 14 as described but shaped to have the particular dimensions discussed above with regard to the tube 16 in order to delimit the column of air as desired. In such embodiment, the body portion 52 of the earplug 50 may include a reinforcing zone or the like proximate the channel 14 to maintain the shape and dimensions of the channel 14 during handling and insertion of the earplug 50. Such reinforcing zone may comprise an area within the plug of increased density, etc., and may be disposed entirely or partially along the length of the channel 14.

Figure 6B:
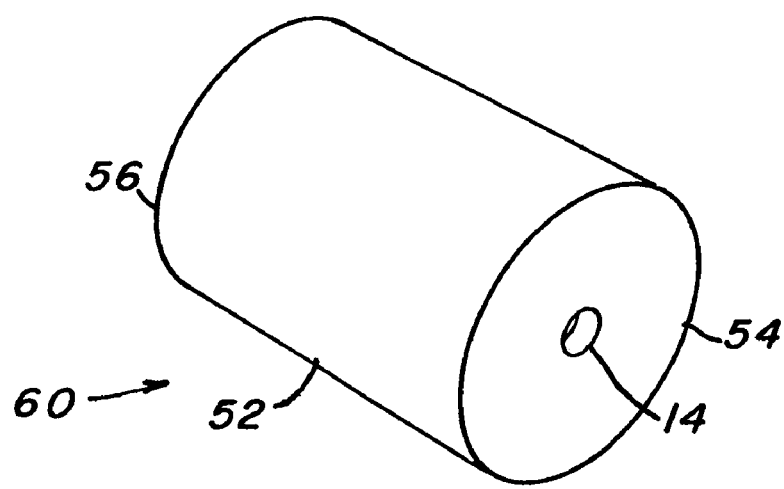
FIGS. 6B and 7B show perspective and cross-section views, respectively, of an earplug in another embodiment of the invention.
Figure 7B:
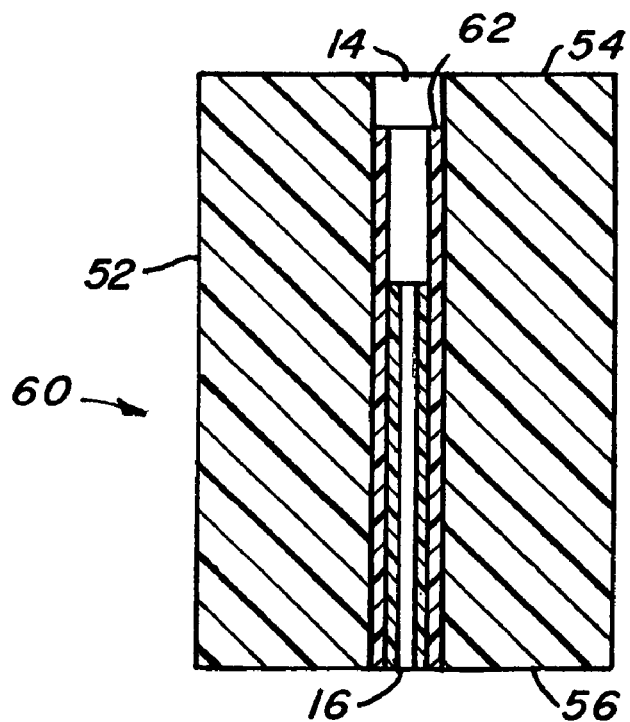

FIGS. 6B and 7B show an earplug 60 in another exemplary embodiment of the invention. The earplug 60 is similar to the earplug 50 in that the former includes the body portion 52, the first end 54, and the second end 56 described above with reference to the earplug 50. However, the channel 14 of the earplug 60 is formed to have a slightly wider diameter than that of the earplug 50.

The wider channel 14 of the earplug 60 receives and retains therein a second tube 62. The second tube 62 preferably includes a diameter slightly larger than the diameter of the channel 14 such that the body portion 52 of the earplug 60 compresses slightly to accommodate the second tube 62 thus creating a firm friction grip of the body portion 52 upon the second tube 62. Alternatively, of course, the second tube 62 may be sized similar to the channel 14 and may be bonded to the earplug 60 with an adhesive, or the material composing the earplug 60 may be formed directly onto and thus bond with the second tube 62, etc.

The tube 16, referred to with regard to the present embodiment as the first tube 16, is disposed within the second tube 62. Here again, the first tube 16 may be frictionally fit within the second tube 62 or alternatively may be bonded to the second tube 62 or formed integrally therewith, etc.

A first end of the second tube 62 extends proximate to the first end 54 of the earplug 60. This first end of the second tube 62 is shown in FIG. 7B as extending beyond a first end of the first tube 16. However, second ends of the first and second tubes 16, 62 are equally disposed generally flush with the second end 56 of the earplug 60. This preferred configuration is, of course, exemplary and may be altered. For example, the first tube 16 may be more centrally located within the earplug body 52 such that the second tube 62 extends beyond both first and second ends of the first tube 16. It is also noted that the distance the second tube 62 extends beyond the first tube 16 at first and/or second ends may vary as desired.

As with the earplug 50 discussed above, the present earplug 60 provides a significant degree of sound attenuation but the first and second tubes 16, 62 extending through the core of the body portion 52, in combination with the remaining portion of the channel 14, delimit a column of air connecting the auditory organs of the inner ear to the outer environment when the earplug 60 is worn by a user. Thus, sound is permitted to travel from the outer environment through the tubes 16, 62 to the inner ear. In this way, the earplug 60 provides the user with a degree of hearing protection while still allowing sound to be heard, thus providing a low attenuation.

The inner diameter $D_I$ of the first tube 16 is approximately 0.005 inch to approximately 0.050 inch: the length L is approximately 0.100 inch to approximately 1.000 inches: and, more particularly, in one exemplary embodiment, the inner diameter $D_I$ is approximately 0.030 inch and the length L is approximately 0.256 inch, and in another embodiment, $D_I$ is approximately 0.020 inch and L is approximately 0.500 inch.

The inner diameter $D_I$ of the second tube 62 is approximately 0.020 inch to approximately 0.090 inch: the length L is approximately 0.100 inch to approximately 1.250 inches: and, more particularly, in a preferred embodiment, the inner diameter $D_I$ is approximately 0.062 inch and the length L is approximately 0.700 inch.

The channel 14 is sized correspondingly with respect to the first and second tubes 16, 62.

The arrangement of the first and second tubes 16, 62 as shown in FIGS. 6B and 7B and as described herein result in the earplug 60 having an increased resistance to compression and pinching of the channel 14. That is, this configuration maintains a consistent column of air through the entire earplug body portion 52, despite pressure exerted upon the channel 14 and/or upon the tubes 16, 62 during, for example, insertion of the earplug into a small ear canal. The first end of the second tube 62 which extends beyond the first tube 16 toward the first end 54 of the earplug 60 maintains the channel 14 beyond the termination of the first tube 16. That is, even if the first end 54 of the earplug 60 is subjected to a compression force, the channel of air created through the body portion 52 will remain open due to the presence of the extending portion of the second tube 62. Additionally, the non-tubed portion of the channel 14, i.e., that portion of the channel without the tubes 16, 62 proximate to the first end 54 of the plug 60, includes a reduced length with respect to the length of the non-tubed portion of the earplug 50. Thus, the earplug 60 includes a reduced exposure of the non-tubed length of the channel 14 and, further, the non-tubed portion which is exposed is more resistant to compression forces because it is buttressed by the immediately adjacent second tube 62.

Accordingly, in the presence of various compression forces, the earplug 60 may maintain a consistent column of air from the first end 54 to the second end 56 by way of the channel 14, the extending portion of the second tube 62, and the first tube 16. Such earplug may be desired, for example, where a wearer has relatively small ear canals and the earplug 60 is thus subjected to considerable compression forces during use or, for example, where the body portion 52 is made of a soft, easily compressible material which may not offer enough resistance during normal use to maintain an open column of air through the plug as desired by the invention.

Figure 8:
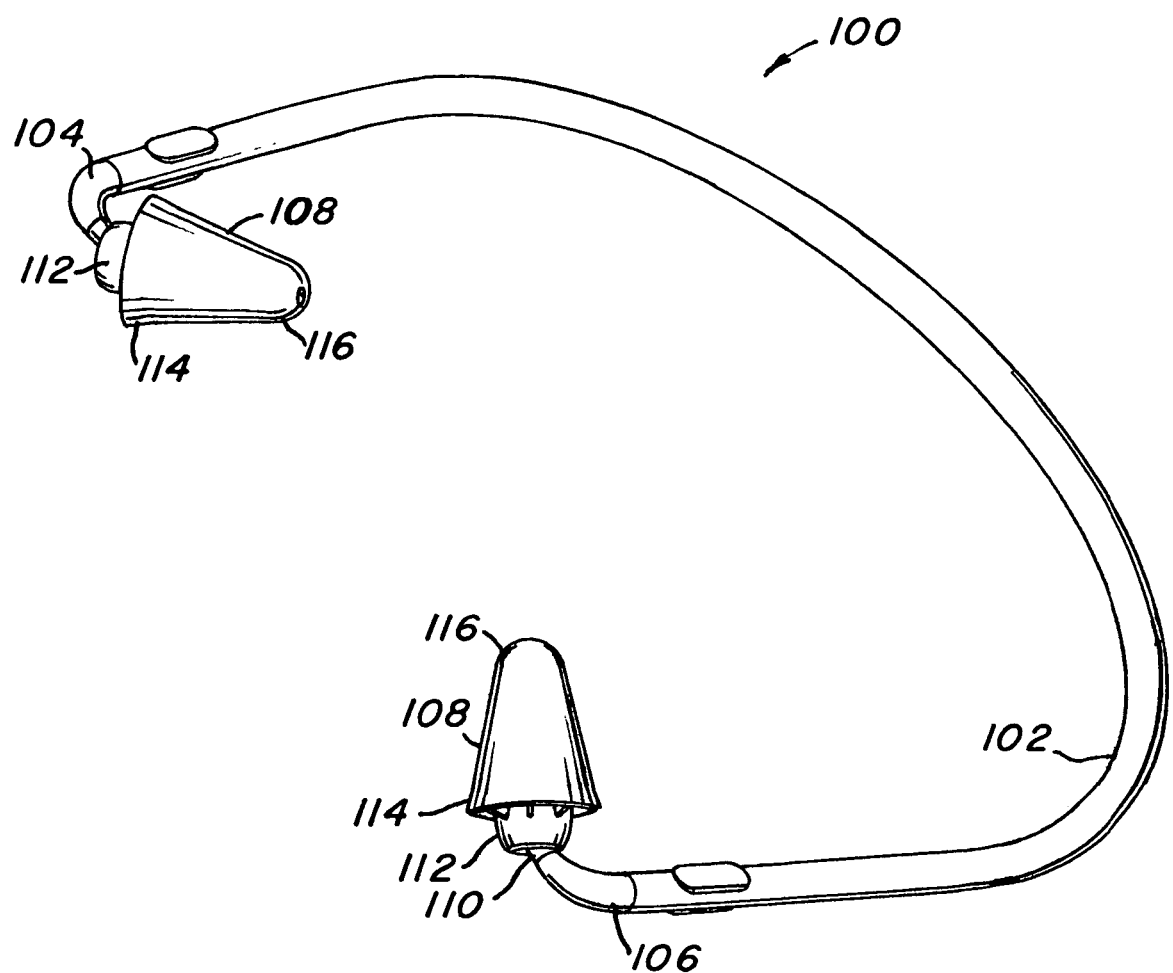
FIG. 8 is a perspective view of a semi-aural hearing protection device.
Figure 9:
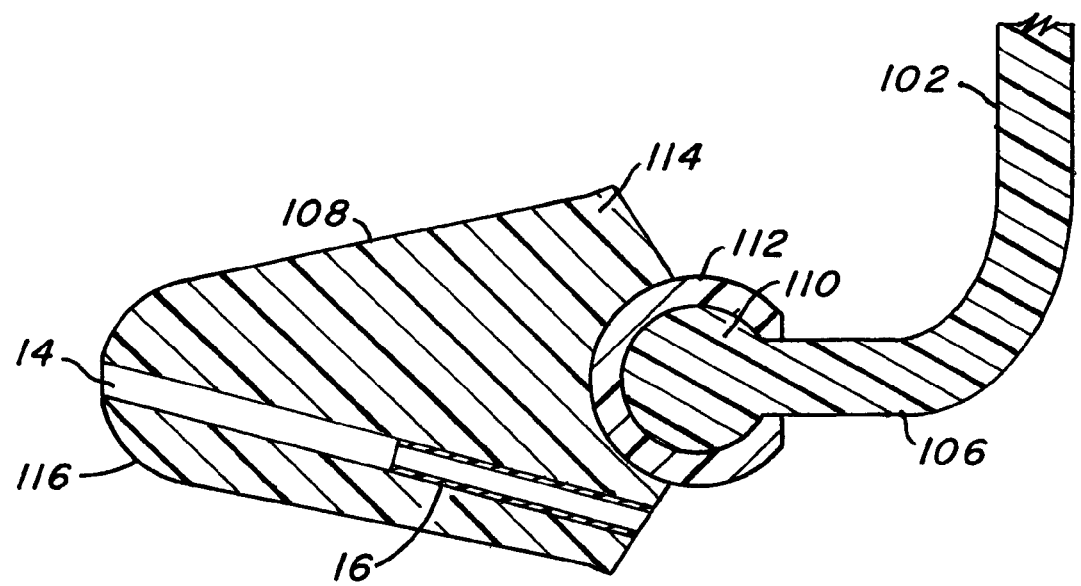
FIG. 9 is an enlarged cross-section view of a portion of the semi-aural device of FIG. 8.
Figure 10:
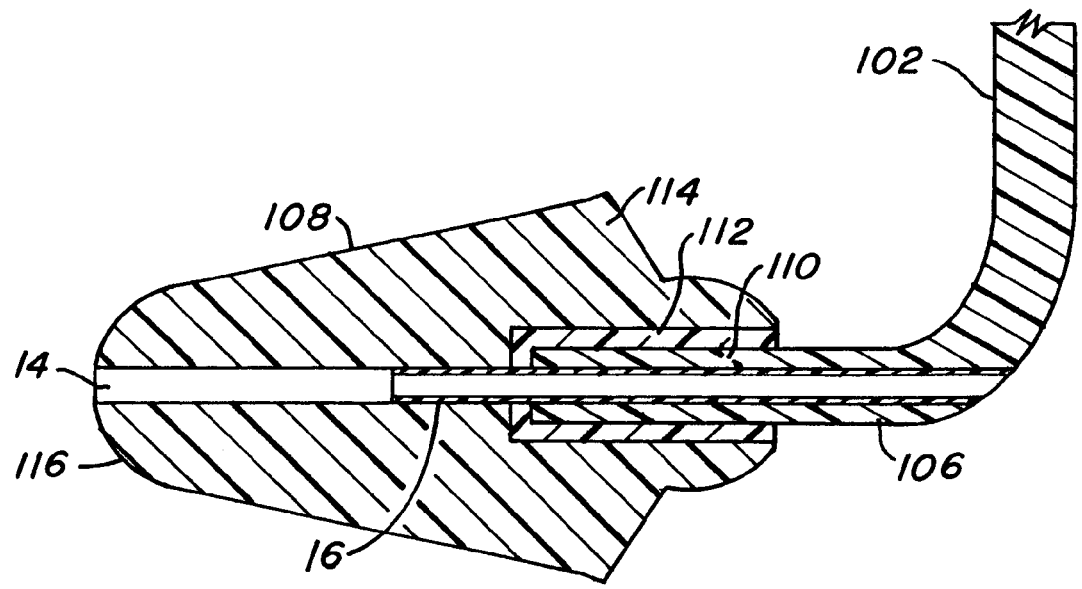
FIG. 10 is an enlarged cross-section view of another embodiment of the portion of the semi-aural device of FIG. 9.

FIGS. 8-10 show a semi-aural device 100 in one embodiment of the invention. The semi-aural device 100 includes a curved neck band 102 having a first end 104 and an opposing second end 106. Sound attenuating elements 108 are disposed at each of the first and second ends 104, 106 of the neck band 102. The neck band 102 includes a connection portion 110 disposed at each of the first and second ends 104, 106. The sound attenuating elements 108 each include a retention portion 112 which receives and retains the connection portion 110 of the neck band 102. The retention portion 112 is disposed at a distal end 114 of each sound attenuating portion 108. The distal end 114 is located opposite an insertion end 116 of the sound attenuating element 108.

In one embodiment, as shown in FIG. 9, the connection portion 110 of the neck band 102 is substantially spherical in shape. The retention portion 112 of the sound attenuating element 108 is correspondingly a hollow spherical form. Accordingly, the combination of the connection portion 110 and the retention portion 112 effectively forms a ball and socket joint which securely attaches the sound attenuating element 108 to the neck band 102 but allows the attenuating element 108 to pivot thereon.

In the embodiment, as shown in FIG. 9, the sound attenuating element 108 further includes the channel 14 and the tube 16 fixed therein. The channel 14 may take any path from the insertion end 116 of the sound attenuating element to the distal end 114 and is show in an exemplary form as linearly traversing the element 108 at an angle to a longitudinal axis of the element 108.

In another embodiment of the semi-aural device 100, as shown in FIG. 10, the connection portion 110 is rod-like in shape and is received and fixably retained within the correspondingly shaped retention portion 112. Here, the connection portion 110 is fixed within the retention portion 112 by friction fit, bonding agent, etc. Thus, the sound attenuating element 108 is held rigidly to the neck band 102. The sound attenuating element 108 of the present embodiment further includes the channel 14 and the tube 16 fixed therein. Here, the channel 14 extends linearly along a longitudinal axis of the sound attenuating element 108 from the insertion end 116 to the distal end 114 and through the retention portion 112, connection portion 110, and through the end 106 of the neck band 102.

Preferably, the sound attenuating elements 108 are formed of a compressible resilient material such as a rubber, a plastic, or a foam-like material. The neck band 102 is composed of a more rigid rubber or plastic material. The tube 16, as described previously, is composed of a rigid or semi-rigid material, such as a rubber or a plastic, in order to maintain the integrity thereof during handling and use of the semi-aural device 100. The tube 16 may extend through the entire described assembly or only through a portion or all of the sound attenuating element 108, as desired. Preferably, as shown in FIGS. 9 and 10, the tube 16 extends only partially into the 14 and is disposed proximate the distal end 114 of the sound attenuating element 108.

In use, the insertion ends 116 of the sound attenuating elements 108 are brought proximate the ear canal opening of a user. The insertion ends 116 are passed through the ear canal opening and the sound attenuating elements 108 are correspondingly pushed into the ear canal wherein they are compressed and lodged into place, effectively attenuating sound.

When the sound attenuating elements 108 are properly inserted, as described, the neck band 102 drapes beneath the chin or across the back of the neck or is placed over the head of the user to support the semi-aural device 100 and to facilitate handling thereof.

The tube 16 extending through the channel 14 of the sound attenuating elements 108 forms the column of air, discussed previously, connecting the inner ear of the user to the outer environment to allow sound to be heard by the user. Thus, the semi-aural device 100 provides attenuation to the user but still allows sounds to be heard, resulting in a low attenuation earplug.

The semi-aural device 100 has been described herein as including the tube 16. However, as discussed with reference to other embodiments of the invention, the semi-aural device may not include the tube 16 and may simply include the channel 14 sized and dimensioned appropriately to form the column of air through the sound attenuating elements for the propagation of sounds. Of course, in such embodiment, certain portions of the sound attenuating elements 108 proximate the channel 14 may be reinforced as desired to maintain the dimensions and shape of the channel 14 during use and handling of the semi-aural device 100.

While the channel 14 and the tube 16 have been shown and discussed herein and throughout as being generally cylindrical in shape and traversing a straight line path (for example, a longitudinal axis of the earplug as shown in FIGS. 2, 4, 6, and 9), the invention clearly contemplates the tube 16 and/or the channel 14 as having any shape and traversing any path sufficient and suitable for creating a pathway for transmission of sound from the outer environment to the auditory organs of the inner ear of the user. For example, the tube 16 and/or the channel 14 may be rectilinear or conical in shape or a combination of cylindrical, rectilinear, and/or conical shapes. The tube 16 and/or the channel 14 may have varying widths of cross-section along its length. Further, the tube 16 and/or the channel 14 may traverse a straight, rectilinear, and/or curvilinear path. For example, the tube 16 and/or the channel 14 may traverse a helical path, etc. In such instances, of course, the column of air would not be a cylindrical column of air, as described previously, but instead would take on the rectilinear or curvilinear shape of the pathway of the tube 16 and/or channel 14.

The earplugs shown and described herein and throughout may further include a stem and/or a cord extending therefrom. The stem and/or cord may be fixed to a surface of the earplug by a bonding agent or the stem and/or cord may be embedded partially in the earplug and thusly fixed thereto. The tube 16 and/or the channel 14 may extend through a portion of the stem and/or cord to complete formation of the column of air required to transmit sound to the inner ear of the user. Alternatively, the tube 16 and/or the channel 14 may diverge from the point of connection of the stem and/or cord and vent at an end of the earplug opposite the insertion end.

The hearing protection device of the invention provides a device, particularly an earplug, which provides a user with a low sound attenuation. The effectiveness of the earplug of the invention was confirmed by Applicant through experimentation, as now described.

To provide end users with information about the amount of sound that a hearing protector will attenuate, products are tested at various frequencies and a determination is made of the amount of attenuation that is provided. To simplify interpretation, a single number rating of those protection levels is normally calculated which is a weighted average of the amount of sound that is attenuated over the series of frequencies tested. In Europe that single number is designated as an SNR. Since the earplugs tested in these examples were tested using the standard specified for Europe, those single numbers which were determined are described as SNR's.

In Applicant's experiments, first, a three-flange push-in type earplug was tested for attenuation properties. The earplug was similar to that shown in FIGS. 1, 2, and 2A but did not include the hole and or tube of the invention. This earplug was exposed to sound of various frequencies ranging from 63 Hz to 8000 Hz. The performance of the earplug was monitored and attenuation data was recorded. Based upon this data, a Single Number Rating (SNR) value of 32 dB was calculated.

Next, a second three-flanged push-in type earplug was tested. This earplug was fitted with a tube extending therethrough as described above with reference to the earplug of FIGS. 1, 2, and 2A. The tube included a length of approximately 0.256 inch and an inner diameter of approximately 0.030 inch. The earplug was then subjected to sound of various frequencies ranging from 63 Hz to 8000 Hz. Attenuation data was recorded and from such data an SNR was found to be 12 dB.

Then, a third three-flanged push-in type earplug was tested. The third earplug included a tube extending therethrough having a length of approximately 0.500 inch and an inner diameter of approximately 0.020 inch. The earplug was then subjected to sound having varying frequencies of 63-8000 Hz, attenuation data was recorded, and an average SNR was found to be 21 dB.

Additionally, it has been found that an earplug including a hole formed entirely therethrough having a diameter greater than the channel/tube diameter of the invention provides near-zero attenuation.

Accordingly, as described in the above-discussed experimentation, the invention enables an earplug which provides a low sound attenuation to a user. Particularly, two instances are described wherein SNRs of 12 dB and 21 dB were achieved by fitting the tested earplug with the channel and tube of the invention. These obtained sound attenuations are significantly less than that provided by the first test earplug which did not have a channel/tube and yielded an SNR of 32 dB. On the other hand, the attenuation of 12 dB and 21 dB provided by the described earplugs is significantly greater than that provided by the mentioned earplug which included a through-hole having a diameter greater than that of the invention resulting in substantially no sound attenuation.

Accordingly, a hearing protection device, particularly an earplug, is provided herein which consistently and effectively provides a low sound attenuation to a user's ear. This is extremely advantageous in situations where a low attenuation is desired since, as shown, most earplugs provide either complete attenuation or near-zero attenuation. Further, the earplug of the invention is easy to manufacture, is cost efficient, and is durable.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A hearing protection device, comprising:
a sound attenuating portion for being disposed within an ear canal of a user to attenuate a passage of sound; and
a channel formed through the sound attenuating portion for allowing sound to pass through the sound attenuating portion, wherein at least a portion of the channel is disposable in the ear canal of the user, wherein at least a portion of the channel has a cross-sectional area and an attenuating diameter or width that is less than a diameter or width in a remainder of the channel, the cross-sectional area and the attenuating diameter or width being configured to attenuate a portion of the sound passing through the channel, wherein the portion of the channel has a distinct first end and a distinct second end, the first end and the second end each being located at a point in the channel where the attenuating diameter or width begins, a point in the channel where the attenuating diameter or width terminates, or at a terminating end of the device itself, the cross-sectional area of the portion being generally consistent across an entirety of the portion from the first end to the second end, wherein the cross-sectional area is also at least partially unobstructed.

2. The hearing protection device of claim 1, wherein the channel extends from a first end of the sound attenuating element to an opposite second end of the sound attenuating element and wherein the channel is substantially unobstructed.

3. The hearing protection device of claim 2, wherein the channel is substantially cylindrical and includes a diameter of approximately 0.005 inch to 0.050 inch and a length of approximately 0.100 inch to 1.000 inch.

4. The hearing protection device of claim 3, wherein the diameter is approximately 0.030 inch and the length is approximately 0.256 inch.

5. The hearing protection device of claim 3, wherein the diameter is approximately 0.020 inch and the length is approximately 0.500 inch.

6. The hearing protection device of claim 2, wherein the channel extends linearly though the sound attenuating element along a longitudinal axis of the hearing protection device or at an angle to the longitudinal axis.

7. The hearing protection device of claim 2, wherein the channel extends non-linearly through the sound attenuating element.

8. The hearing protection device of claim 2, wherein the first end is disposed in the ear canal and the second end extends from the ear canal when the hearing protection device is worn by the user.

9. The hearing protection device of claim 2, further comprising a rigid or semi-rigid stem portion disposed at the second end of the sound attenuating element wherein the channel extends into and through at least a part of the stem portion.

10. The hearing protection device of claim 9, wherein the channel extends linearly though the sound attenuating element and linearly through the stem along a longitudinal axis of the hearing protection device.

11. The hearing protection device of claim 2, wherein the sound attenuating portion is a tube disposed in the channel, the tube including attenuating diameter that is consistent from the first end of the tube to the second end of the tube.

12. The hearing protection device of claim 11, wherein the tube includes a circular cross-section and extends through the channel from an interior the sound attenuating element where the attenuating diameter or width begins to the terminating end of the device.

13. The hearing protection device of claim 12, wherein the tube includes an inner diameter of approximately 0.005 inch to 0.050 inch and a length of approximately 0.100 inch to 1.000 inch.

14. The hearing protection device of claim 13, wherein the inner diameter is approximately 0.030 inch and the length is approximately 0.256 inch.

15. The hearing protection device of claim 13, wherein the inner diameter is approximately 0.020 inch and the length is approximately 0.500 inch.

16. The hearing protection device of claim 11, wherein the tube is fixed to the device at the channel by a bonding agent and/or by a friction fit.

17. The hearing protection device of claim 11, wherein a width of the tube is larger than a width of the channel such that the tube is fixed within the channel by the friction fit.

18. The hearing protection device of claim 9, further comprising a tube disposed in the channel and extending through the sound attenuating and through the stem to an opening at a surface of the stem opposite the sound attenuating element.

19. The hearing protection device of claim 1, further comprising a reinforcement portion disposed in the sound attenuating element proximate the channel to reinforce and maintain a size and shape of the channel during a use of the device.

20. The hearing protection device of claim 1, wherein the sound attenuating element comprises an elongate stalk member and a plurality of hollow, rearwardly facing flanges of substantially hemispherical shape, the flanges extending generally radially from the stalk member.

21. The hearing protection device of claim 20, wherein the stalk member comprises a nose end and an opposing distal end, and wherein the plurality of flanges comprises at least three flanges of serially increasing diameters disposed at spaced intervals along the stalk member, the flange having a smallest diameter being disposed at the nose end.

22. The hearing protection device of claim 20, wherein the channel is formed through the stalk member, from a nose end to an opposite distal end, along a longitudinal axis of the device, and wherein the channel is cylindrical in shape and includes openings at the nose end of the stalk member and at the distal end.

23. The hearing protection device of claim 22, wherein the channel includes a diameter of approximately 0.005 inch to 0.050 inch and a length of approximately 0.100 inch to 1.000 inch.

24. The hearing protection device of claim 23, wherein the diameter is approximately 0.030 inch and the length is approximately 0.256 inch.

25. The hearing protection device of claim 23, wherein the inner diameter is approximately 0.020 inch and the length is approximately 0.500 inch.

26. The hearing protection device of claim 22, further comprising a tube disposed in the channel and extending through the stalk member from the nose end to the distal end.

27. The hearing protection device of claim 26, wherein the tube includes an inner diameter of approximately 0.005 inch to 0.050 inch and a length of approximately 0.100 inch to 1.000 inch.

28. The hearing protection device of claim 27, wherein the inner diameter is approximately 0.030 inch and the length is approximately 0.256 inch.

29. The hearing protection device of claim 27, wherein the inner diameter is approximately 0.020 inch and the length is approximately 0.500 inch.

30. The hearing protection device of claim 27, wherein the tube is fixed to the device at the channel by a bonding agent and/or wherein a width of the tube is larger than a width of the channel such that the tube is fixed within the channel by the friction fit.

31. The hearing protection device of claim 1, wherein the sound attenuating element is a compressible resilient foam member including an insertion end and an opposite distal end, the device further comprising a stem member fixed at a first end to the distal end of the foam member and extending therefrom to a second end.

32. The hearing protection device of claim 31, wherein the channel extends linearly along a longitudinal axis of the hearing protection device from the insertion end of the foam member, through the foam member to the distal end, and through the stem member to an opening at the second end of the stem member.

33. The hearing protection device of claim 32, wherein the channel is substantially cylindrical, the device flirt her comprising a cylindrical tube disposed in the channel extending from the insertion end of the foam member to the second end of the stem member.

34. The hearing protection device of claim 33, wherein the channel includes an outer diameter larger than a diameter of the channel such that the tube is fixed in the channel by a friction fit and wherein the tube includes an inner diameter of approximately 0.050 inch to 0.050 inch and a length of approximately 0.100 inch to 1.000 inch.

35. The hearing protection device of claim 1, wherein the sound attenuating element comprises a compressible resilient member having a substantially cylindrical shape and opposing first and second ends.

36. The hearing protection device of claim 35, wherein the channel extends through the compressible resilient member from the first end to the second end along a longitudinal axis of the hearing protection device.

37. The hearing protection device of claim 36, wherein the channel is substantially cylindrical, the device further comprising a cylindrical tube disposed in the channel extending from the first end to the second end.

38. The hearing protection device of claim 37, wherein the channel includes an outer diameter larger than a diameter of the channel such that the tube is fixed in the channel by a friction fit and wherein the tube includes an inner diameter of approximately 0.005 inch to 0.050 inch and a length of approximately 0.100 inch to 1.000 inch.

39. The hearing protection device of claim 1, further comprising a cord connecting the sound attenuating element to a second sound attenuating element.

40. The hearing protection device of claim 1, further comprising a substantially U-shaped band connecting the sound attenuating element to a second sound attenuating element.

41. The hearing protection device of claim 1, further comprising:
 a first tube disposed in the channel; and
 a second tube disposed in the channel,
 wherein the first tube is disposed at least partially within the second tube.

42. The hearing protection device of claim 41, wherein the second tube includes a length less than a length of the channel and the first tube includes a length less than the length of the first tube, the first tube being contained entirely within the second tube, the second tube extending within the channel beyond the first tube.

43. The hearing protection device of claim 42, wherein an inner diameter of the first tube is about 0.030 inch and an inner diameter of the second tube is about 0.060 inch.

44. The hearing protection device of claim 41, wherein the sound attenuating portion is a foam and the channel extends along a longitudinal axis of the foam.

45. The hearing protection device of claim 1, wherein the channel is cylindrical in cross-section having a plurality of diameters over a length of the channel.

46. The hearing protection device of claim 45, wherein the plurality of diameters are formed by a corresponding plurality of differently sized tubes disposed within the channel.

47. The hearing protection device of claim 1, wherein the channel is generally cylindrical in cross-section.

48. A hearing protection device, comprising:
 an elongated stalk member having opposing first and second ends;
 a plurality of hollow, rearwardly extending flange elements of substantially circular cross-sections and of serially increasing diameters disposed along the stalk member, a smallest of said flange elements being disposed proximate said first end; and a channel formed along a longitudinal axis of the hearing protection device from a first opening at the first end of the stalk member to a second opening at the second end of the stalk member;

wherein the flanges compress upon the stalk member when the hearing protection device is insertable into an ear canal of a user to attenuate a passage of sound through the ear canal; and wherein the channel allows sound to pass through the hearing protection device, wherein at least a portion of the channel is disposable in the ear canal of the user, wherein at least a portion of the channel has a cross-sectional area and an attenuating diameter or width that is less than a diameter or width in a remainder of the channel, the cross-sectional area and the attenuating diameter or width being configured to attenuate a portion of the sound passing through the channel, wherein the portion of the channel has a distinct first end and a distinct second end, the first end and the second end each being located at a point in the channel where the attenuating diameter or width begins, a point in the channel where the attenuating diameter or width terminates, or at a terminating end of the device itself, the cross-sectional area of the portion being generally consistent across an entirety of the portion from the first end to the second end, wherein the cross-sectional area is also at least partially unobstructed.

49. The hearing protection device of claim 48, further comprising a tube extending through the device disposed at the channel, wherein the tube includes an inner diameter of approximately 0.005 inch to 0.050 inch and a length of approximately 0.100 inch to 1.000 inch.

50. The hearing protection device of claim 49, wherein the inner diameter is approximately 0.030 inch and the length is approximately 0.256 inch or the inner diameter is approximately 0.020 inch and the length is approximately 0.500 inch.

51. A method of manufacturing a hearing protection device, comprising:

forming a sound attenuating element of a compressible resilient material, the element having opposing first and second ends; and forming a channel through the sound attenuating element from the first end to the second end, wherein at least a portion of the channel is disposable in the ear canal of the user, wherein at least a portion of the channel has a cross-sectional area and an attenuating diameter or width that is less than a diameter or width in a remainder of the channel, the cross-sectional area and the attenuating diameter or width being configured to attenuate a portion of sound that passes through the channel, wherein the portion of the channel has a distinct first end and a distinct second end, the first end and the second end each being located at a point in the channel where the attenuating diameter or width begins, a point in the channel where the attenuating diameter or width terminates, or at a terminating end of the device itself, the cross-sectional area of the portion being generally consistent across an entirety of the portion from the first end to the second end, wherein the cross-sectional area is also at least partially unobstructed; and inserting a tube into the channel.

52. The method of manufacturing of claim 51, further comprising:

sizing the tube to include a diameter greater than a diameter of the channel such that said inserting establishes a friction fit of the tube within the channel.

53. The method of claim 51, further comprising inserting a second tube into the channel such that the first tube is disposed within the second tube and the second tube includes a length greater than a length of the first tube.

54. A hearing protection device, comprising:

a sound attenuating portion for being disposed within an ear canal of a user to attenuate a passage of sound; and a channel formed through the sound attenuating portion for allowing sound to pass through the sound attenuating portion, wherein at least a portion of the channel is disposable in the ear canal of the user, and wherein the channel is formed of a substantially non-compressible material, such that the channel remains open during normal use of the device, and wherein at least a portion of the channel has a cross-sectional area and an attenuating diameter or width that is less than a diameter or width in a remainder of the channel, the cross-sectional area and the attenuating diameter or width being configured to attenuate a portion of sound that passes through the channel, wherein the portion of the channel has a distinct first end and a distinct second end, the first end and the second end each being located at a point in the channel where the attenuating diameter or width begins, a point in the channel where the attenuating diameter or width terminates, or at a terminating end of the device itself, the cross-sectional area of the portion being generally consistent across an entirety of the portion from the first end to the second end.

\* \* \* \* \*

UNITED STATES PATENT AND TRADEMARK OFFICE
CERTIFICATE OF CORRECTION

PATENT NO. : 7,697,706 B2  Page 1 of 1
APPLICATION NO. : 10/700213
DATED : April 13, 2010
INVENTOR(S) : Marc L. Doty It is certified that error appears in the above-identified patent and that said Letters Patent is hereby corrected as shown below:

Column 10
Line 4, delete "inch:" and insert -- inch; --, therefor.
Line 5, delete "inches:" and insert -- inches; --, therefor.
Line 12, delete "inch:" and insert -- inch; --, therefor.
Line 13, delete "inches:" and insert -- inches; --, therefor.

Column 14
Line 21, in Claim 6, delete "though" and insert -- through --, therefor.
Line 38, in Claim 10, delete "though" and insert -- through --, therefor.

Column 15
Line 67, in Claim 33, delete "flirt her" and insert -- further --, therefor.

Column 16
Line 8, in Claim 34, after "approximately" delete "0.050" and insert -- 0.005 --, therefor.

Signed and Sealed this

Twenty-sixth Day of October, 2010

David J. Kappos
*Director of the United States Patent and Trademark Office*